United States Patent [19]

Yokoyama et al.

[11] Patent Number: 5,239,108
[45] Date of Patent: Aug. 24, 1993

[54] PROCESS FOR PRODUCING ALIPHATIC OR ALICYCLIC ALDEHYDE

[75] Inventors: Toshiharu Yokoyama; Naoko Matsuyama; Takao Maki, all of Kanagawa, Japan

[73] Assignee: Mitsubishi Kasei Corporation, Tokyo, Japan

[21] Appl. No.: 963,527

[22] Filed: Oct. 20, 1992

Related U.S. Application Data

[63] Continuation of Ser. No. 643,612, Jan. 22, 1991, abandoned.

[30] Foreign Application Priority Data

Jan. 22, 1990 [JP] Japan ................................. 2-12233

[51] Int. Cl.$^5$ ...................... C07C 45/41; C07C 67/30; C07C 67/327
[52] U.S. Cl. .................................... 560/126; 560/177; 568/484; 568/446; 568/449; 568/443
[58] Field of Search ............... 568/648, 650, 443, 446, 568/449, 484; 560/126, 177; 260/405

[56] References Cited

U.S. PATENT DOCUMENTS 4,613,700  9/1986  Maki et al. .......................... 568/435

FOREIGN PATENT DOCUMENTS 0150961  7/1985  European Pat. Off. .
62-14942  1/1987  Japan .
62-108832  5/1987  Japan .

OTHER PUBLICATIONS

Patent Abstracts of Japan, vol. 11, No. 192, abstract of JP-A-62 14 942.
Patent Abstracts of Japan, vol. 9, No. 317, abstract of JP-A-60 152 434.
Patent Abstracts of Japan, vol. 11, No. 322, abstract of JP-A-62 108 832.

*Primary Examiner*—Marianne M. Cintins
*Assistant Examiner*—Margaret J. Page
*Attorney, Agent, or Firm*—Sughrue, Mion, Zinn, Macpeak & Seas

[57] ABSTRACT

A process for producing an aliphatic or alicyclic aldehyde is disclosed, which process comprises the step of hydrogenating an aliphatic or alicyclic carboxylic acid or a derivative thereof with molecular hydrogen in the presence of a catalyst, wherein the catalyst is a zirconium oxide catalyst which contains chromium as an essential component, has a weakly basic site amount of more than 0.03 mmol/g as determined by a temperature programmed desorption method using carbon dioxide as an adsorbate in which the amount of carbon dioxide desorbed in the temperature range of from 100° to 250° C. is measured, and has pores having a radius of from 20 to 500 Å in an amount of not less than 0.1 cc/g and pores having a radius of from 1,000 to 50,000 Å in an amount of not less than 0.05 cc/g as measured with a mercury porosimeter. Aldehydes can be obtained directly from aliphatic or alicyclic carboxylic acids or derivatives thereof in high yield.

11 Claims, No Drawings

PROCESS FOR PRODUCING ALIPHATIC OR ALICYCLIC ALDEHYDE

This is a continuation of application Ser. No. 07/643,612 filed Jan. 22, 1991 now abandoned.

FIELD OF THE INVENTION

The present invention relates to a process for producing an aliphatic or alicyclic aldehyde which is useful as an intermediate in organic syntheses.

BACKGROUND OF THE INVENTION

While various processes for producing aliphatic aldehydes have been proposed to date, an optimal means for starting with carboxylic acids or derivatives thereof have not yet been reported.

The most commonly employed of the conventional processes is a process utilizing so-called Rosenmund reduction of a carboxylic acid chloride. This process has a disadvantage of high cost incurred.

Direct reduction of carboxylic acids with molecular hydrogen would be the most advantageous process for the production of aldehydes, but it has been regarded extremely difficult.

As the latest technique, U.S. Pat. No. 4,328,373 proposes a process in which methyl isobutyrate or methyl pivalate is hydrogenated in a gaseous phase in the presence of a yttrium oxide catalyst to obtain a corresponding aldehyde. This process, however, starts with a methyl ester of a carboxylic acid not with a free carboxylic acid. Moreover, the temperature employed is high throughout the reaction, and the yield of a desired aldehyde is low due to side reactions.

The present inventors previously proposed a process in which an aliphatic carboxylic acid is hydrogenated in the presence of zirconium oxide as a catalyst to obtain a corresponding aldehyde as disclosed in JP-A-62-108832 (the term "JP-A" as used herein means an "unexamined published Japanese patent application"). As a result of further investigations, however, it turned out that a zirconium oxide catalyst which is prepared by conventional processes needs further improvements to be used in the above-described process, for example, in activity, yield of desired products, working life, etc. In particular, when the starting aliphatic carboxylic acid has a large number of carbon atoms, the yield attained is low.

SUMMARY OF THE INVENTION

An object of the present invention is to provide a process for producing an aliphatic or alicyclic aldehyde in high yield directly from a corresponding aliphatic or alicyclic carboxylic acid or a derivative thereof.

Other objects and effects of the present invention will be apparent from the following description.

The present invention relates to a process for producing an aliphatic or alicyclic aldehyde comprising the step of hydrogenating an aliphatic or alicyclic carboxylic acid or a derivative thereof with molecular hydrogen in the presence of a catalyst, wherein the catalyst is a zirconium oxide catalyst which contains chromium as an essential component, has a weakly basic site amount of more than 0.03 mmol/g as determined by a temperature programmed desorption method using carbon dioxide as an adsorbate in which the amount of carbon dioxide desorbed in the temperature range of from 100° to 250° C. is measured, and has pores having a radius of from 20 to 500 Å in an amount of not less than 0.1 cc/g and pores having a radius of from 1,000 to 50,000 Å in an amount of not less than 0.05 cc/g as measured with a mercury porosimeter.

DETAILED DESCRIPTION OF THE INVENTION

It is known that acid-base characteristics of zirconium oxide solid catalysts containing chromium as an essential component are subject to wide variations depending on impurity contents in raw materials, methods of preparation, and the like.

Various means for determining acid-base characteristics of a solid are known. Inter alia, an indicator adsorption method (*Yuki Gosei Kaoaku Kyokai-shi* (Journal of The Society of Synthetic Organic Chemistry, Japan), Vol. 33, No. 11, p. 842 (1975)) is commonly used. However, this method is unsuitable for determining colored substances such as the catalyst used in the present invention.

On the other hand, there is a method for examining acid-base characteristics of a solid catalyst in which a basic gas, e.g., ammonia, or an acidic gas, e.g., carbon dioxide, is once adsorbed on the surface of a solid, then desorbing the adsorbed gas by increasing a temperature at a given rate, and the amount of desorbed gas is measured, known as a temperature programmed desorption method (*Shokubai Koza* (Lecture on Catalyst), Vol. 3, pp. 145-156, published by Kodansha, Japan on 1985.

According to this method, characteristics of basic sites or acidic sites on the catalyst surface can be determined by using carbon dioxide or ammonia gas as an adsorbate molecule, respectively. That is, the temperature at which the gas is desorbed shows strength, and the amount of desorbed gas shows the amount of acidic sites or basic sites.

The present inventors have investigated various zirconium oxide catalysts essentially containing chromium according to the above-mentioned temperature programmed desorption method and, as a result, found that the amount of weakly basic sites on the catalyst surface (hereinafter referred to as "weakly basic site amount") relates to the activity of the catalyst. Namely, it was elucidated that, the amount of carbon dioxide desorbed in the temperature range of from 100° to 250° C. in a temperature programmed desorption method using carbon dioxide being taken as a weakly basic site amount, a catalyst having a weakly basic site amount of more than 0.03 mmol/g is particularly excellent in catalyzing activity.

In determining weakly basic sites on the surface of a solid catalyst by a temperature programmed desorption method, the absolute adsorption and desorption amounts of carbon dioxide vary depending on the apparatus or operation used. On this account, the present inventors determined, for reference, a weakly basic site amount of standard active alumina ALO-4 specified by Catalysis Society of Japan under the same conditions for a temperature programmed method. As a result, ALO-4 was found to have a weakly basic site amount of 0.03 mmol/g or less. Accordingly, the catalyst which can be used in the present invention is characterized by having a greater weakly basic site amount than ALO-4.

The carbon dioxide desorbed and analyzed in such a low temperature range of from 100° to 250° C. is the one having been adsorbed onto weakly basic sites on the catalyst surface.

If the weakly basic site amount is 0.03 mmol/g or less, the reaction results of hydrogenation particularly of aliphatic carboxylic acids are considerably deteriorated.

It appears that various factors account for the basic characteristics of the catalyst as above determined. In particular, presence of impurities have a great influence. For example, where zirconium oxide catalyst is prepared by refining raw ore, impurities such as sulfur and halogens sometimes remain depending on the process employed. These impurities cause wide variations of acid-base characteristics of the surface of the resulting catalyst. The same is applied to chromium raw materials used as an essential component.

Therefore, in the preparation of the catalyst to be used in the present invention, it is required to purify raw materials of zirconium oxide catalyst and chromium compounds.

Raw materials of zirconium oxide catalyst which can be used in the present invention include commercially available zirconium hydroxide (e.g., zirconyl hydroxide, zirconium hydroxide) and zirconyl carbonate. Commercially available zirconium oxide is also employable as a raw material.

An impurity-free zirconium oxide catalyst can be obtained by firing granules of the raw material, e.g., commercially available zirconium oxide, zirconyl hydroxide, zirconium hydroxide, zirconyl carbonate, etc. Use of commercially available zirconium oxide is not recommended as the raw material because it may contain co-fired impurities on the surface thereof which are difficult to be removed. Therefore, zirconium oxide catalyst prepared by firing the raw material, such as zirconium hydroxide, zirconyl hydroxide or zirconyl carbonate, at a temperature of from about 300° to 950° C. prior to molding is preferred. More preferably, firing of these raw materials is conducted after molding. When the raw materials of zirconium oxide catalyst are used for the preparation of a catalyst, since the amount of impurities, e.g., sulfur and halogens, more or less differs depending on the process for preparing the raw material itself, zirconium oxide catalyst which has been prepared from the raw materials containing large amounts of impurities is not suitable in the present invention.

It is preferred that, if desired, impurity contents of raw materials can be reduced before molding or firing by known methods, such as washing with water or diluted aqueous ammonia.

It is particularly necessary to reduce a sulfur content in the raw material to 0.1% by weight or less because sulfur is present as a sulfuric acid ion and seriously reduces the weakly basic site amount on the catalyst surface.

Chromium compounds which can be used in the preparation of the catalyst include inorganic chromium compounds, e.g., chromium sulfate, chromium nitrate, chromium halides, and chromium (VI) oxide, bichromic acid or an ammonium or alkali metal salt thereof; and organic chromium salts, e.g., chromium formate, chromium acetate, and chromium oxalate. On an account of containing no general catalyst poisons, preferred of them are those which decompose at relatively low temperatures and containing no other poisoning elements, such as chromium nitrate, chromium anhydride salts, ammonium bichromate, chromium acetate, chromium formate, and chromium oxalate.

The atomic ratio of chromium to zirconium (Cr/Zr) in the catalyst of the present invention ranges from about 0.001 to about 0.5, and preferably from 0.01 to 0.3.

In the process of the present invention, catalytic activity is closely related to the volume and distribution of pores. It is required for the catalyst to have not less than 0.1 cc/g of pores having a radius of from 20 to 500 Å and not less than 0.05 cc/g of pores having a radius of from 1,000 to 50,000 Å.

If the volume of pores having a radius of from 1,000 to 50,000 Å is less than 0.05 cc/g, diffusion of the reactant and reaction product in pores is considerably retarded even if other requirements, i.e., weakly basic site amount and volume of pores having a radius of from 20 to 500 Å, are satisfied. Such being the case, the reaction activity is reduced, and the product undergoes successive reactions, resulting in a reduction in aldehyde selectivity.

The catalyst according to the present invention can be prepared in a conventional manner. For example, a chromium salt aqueous solution and zirconyl hydroxide powder are mixed, if desired, in the presence of an appropriate binder, and the mixture is extrusion-molded, dried, and fired at a prescribed temperature. This process being followed, a pore distribution and a pore volume can be appropriately adjusted by dehydration and decomposition of raw materials during drying and firing and, if desired, removal of organic binders added (e.g., polyvinyl alcohol, starch paste, crystalline cellulose, various surface active agents, and low-melting waxes) by combustion.

It should be noted that tablet compressing method, which is a commonly employed molding technique for solid catalysts, is not favorable in the present invention because it causes destruction of pores having a radius of from 1,000 to 50,000 Å. It is a matter of course that the tablet compressing method can be employed as far as the volume of pores having a radius of from 1,000 to 50,000 Å may be maintained at 0.05 cc/g or more by using an organic binder removable by combustion.

Binders which may be added if desired preferably include organic compounds which disappear on firing. Inorganic binders tend to remain on the catalyst surface after firing, adversely affecting reaction activity. Preferred organic binders include those generally employed for granulation, such as polyvinyl alcohol, starch paste, crystalline cellulose, surface active agents, low-melting waxes, and stearic acid.

A preferred temperature for firing granules ranges from 400° to 1,100° C., and more preferably from 400° to 900° C.

Carboxylic acids which can be used as a starting material in the process of the present invention include aliphatic carboxylic acids, alicyclic carboxylic acids, and derivatives of these carboxylic acids. Preferred derivatives include esters and anhydrides.

Specific examples of the aliphatic carboxylic acids include straight chain or branched and saturated or unsaturated carboxylic acids having from 4 to 24 carbon atoms, such as butyric acid, isobutyric acid, pivalic acid, valeric acid, hexanoic acid, heptanoic acid, octanoic acid, 2-ethylhexanoic acid, nonanoic acid, decanoic acid, undecanoic acid, lauric acid, tridecanoic acid, tetradecanoic acid, pentadecanoic acid, hexadecanoic acid, heptadecanoic acid, stearic acid, isostearic acid, nonadecanoic acid, eicosanoic acid, heneicosanoic acid, docosanoic acid, tricosanoic acid, tetracosanoic acid, 10-undecenoic acid, oleic acid, and 11-eicosenoic acid.

Specific examples of the alicyclic carboxylic acids include cyclopentanecarboxylic acid and cyclohexanecarboxylic acid.

These aliphatic or alicyclic carboxylic acids may be substituted with reaction inert groups, such as an aryl group and an alkoxy group.

Carboxylic acid derivatives which can be used as a starting compound include esters, such as methyl, ethyl, n-butyl, cyclohexyl, and phenyl esters; anhydrides, such as homoanhydride and heteroanhydrides; and the like. Specific examples of these derivatives include methyl laurate, n-butyl laurate, methyl stearate, n-butyl stearate, lauric anhydride, and stearic anhydride.

In the present invention, a carboxylic acid containing from 4 to 24 carbon atoms or a derivative thereof is generally used as a starting compound. Considering that the catalyst to be used has pores of from 1,000 to 50,000 Å in radius and that such a pore size distribution is related to diffusion of the starting material and the reaction product as stated above, the present invention exhibits particularly pronounced effects when applied to compounds having a relatively large-sized molecule, i.e., higher aliphatic carboxylic acids having from about 8 to about 22, and particularly from 12 to 22, carbon atoms.

Hydrogenation is carried out in a gaseous phase to advantage. The reaction temperature is generally from about 200° to about 500° C., and preferably from 250° to 400° C. The reaction pressure is generally normal pressure or, if desired, under slight pressure.

Where the catalyst is used as a fixed bed, the starting carboxylic acid or its derivative is generally fed 3 at a space velocity ranging from about 0.01 to about 1 hr$^{-1}$, and preferably from 0.03 to 0.5 hr$^{-1}$, in terms of LHSV (liquid hourly space velocity).

The space velocity of hydrogen is generally in the range of from about 100 to about 20,000 hr$^{-1}$, and preferably from 500 to 5,000 hr$^{-1}$, in terms of GHSV (gas hourly space velocity). Hydrogen to be fed may contain small amounts of inert gases such as nitrogen, water vapor, and carbon ioxide.

The present invention is now illustrated in greater detail by way of the following Examples and Comparative Examples, but it should be understood that the present invention is not deemed to be limited thereto. All the percents, parts, and ratios are by weight unless otherwise indicated.

EXAMPLE 1 AND COMPARATIVE EXAMPLES 1 AND 2

Preparation of Catalysts

Catalyst A (Example 1)

Commercially available zirconyl hydroxide was thoroughly washed with diluted aqueous ammonia and water to remove impurities and dried. To 2,340 g of the thus treated zirconyl hydroxide (ZrO(OH)$_2$, ZrO$_2$ contents: 85.4%) was added an aqueous solution consisting of 325 g of chromium nitrate nonahydrate, 50 g of polyvinyl alcohol ("EG05" produced by Nippon Gosei K.K.), and 940 g of water, and the mixture was kneaded in a kneader and extruded by means of an extrusion molding machine to obtain a strand having a diameter of 3 mm. The extruded strand was cut to a length of about 5 mm, dried, and fired at 700° C. for 3 hours to obtain a catalyst (designated catalyst A). The sulfur content of catalyst A was found to be 0.02%.

Catalyst B (Comparative Example 1)

Catalyst B was prepared in the same manner as for catalyst A, except for using commercially available zirconyl hydroxide as such without removing impurities. Catalyst B had a sulfur content of 0.2%.

Catalyst C (Comparative Example 2)

The same raw materials at the same mixing ratio as used for catalyst A were kneaded, dried, and fired at 600° C. for 3 hours. One part of stearic acid was mixed with 100 parts of the fired product, and the mixture was formed into tablets having a diameter of 5 mm and a length of 5 mm by the tablet compressing method. The tablets were fired at 700° C. for 3 hours to prepare catalyst C.

Determination of Physical Properties of Catalysts

1) Surface Basicity

Surface basicity of catalysts A, B and C was determined by a temperature programmed desorption method using carbon dioxide as an adsorbate. The determination was made in accordance with a standard method described in *Shokubai Jikken Handbook* (Catalyst Experimental Handbook), separate volume of *Shokubai Koza* (Lectures on Catalyst), p. 175, published by Kodansha, Japan on 1986 as follows.

The catalyst was ground to 10 to 20 mesh, and a 20 mg portion was placed in a U-tube made of quartz (inner diameter: 3 mm). The U-tube was set in an apparatus, the atmosphere was displaced with helium gas, and the catalyst was heated at 600° C. for 1 hour. The catalyst was then reduced with hydrogen at 350° C. for 1 hour while feeding 50 ml/min of H$_2$ gas. The temperature was lowered to 100° C., and the tube was purged with helium gas. Pulses (1 ml) of helium gas containing 10% carbon dioxide were introduced at 100° C. until adsorption saturation was reached, followed by purging with helium gas. The temperature was raised up to 600° C. at a rate of 10° C./min while feeding 40 ml/min of helium gas, and desorbed gas was analyzed by means of a thermal conductivity cell to obtain a chromatogram. The above-described operation was repeated, except that carbon dioxide was not adsorbed to obtain a base line which should be subtracted from the resulting chromatogram.

For reference, surface basicity of high-purity active alumina, ALO-4, specified by Catalysis Society of Japan (specific surface area: 177 m$^2$/g) was also determined in the same manner as described above.

2) Pore Volume (ml/g)

Measured with a mercury porosimeter.

3) Specific Surface Area

Measured in accordance with a BET method.

The results of these physical properties determinations are shown in Table 1 below. As shown in Table 1, catalysts A, B and C had substantially the same specific surface area (about 70 m$^2$/g) but differed in surface base site amount and pore structure.

Hydrogenation of Lauric Acid

Hydrogenation of lauric acid was carried out at a varied reaction temperature using a given amount of catalyst A, B or C under the following conditions.
Pressure: normal pressure Space Velocity of Acid (LHSV): 0.14 hr$^{-1}$
Space Velocity of Hydrogen (GHSV): 1,250 hr$^{-1}$ The yield of lauric aldehyde was obtained by multiplying (conversion of lauric acid) by (selectivity of lauric aldehyde). The conversion of lauric acid (%), selectivity of lauric aldehyde (%), and space time yield of lauric aldehyde (mol/kg-catalyst·hr) obtained under the temperature condition which gave the maximum yield as obtained above are shown in Table 1.

TABLE 1

| Catalyst | | $CO_2$ Desorption at 100–250° C. (mmol/g-catalyst) | Pore Volume (ml/g) | | Specific Surface Area (m²/g) | Reaction Temperature (°C.) | Conversion of Lauric Acid (%) | Selectivity of Lauric Aldehyde (%) | Space Time Yield of Lauric Aldehyde |
|---|---|---|---|---|---|---|---|---|---|
| | | | 20–500 Å | 1,000–50,000 Å | | | | | |
| Example 1 | A | 0.080 | 0.18 | 0.19 | 72 | 325 | 89 | 85.2 | 0.525 |
| Comparative Example 1 | B | 0.014 | 0.18 | 0.18 | 69 | 360 | 92.8 | 77.6 | 0.423 |
| Comparative Example 2 | C | 0.080 | 0.17 | 0.04 | 77 | 350 | 80.5 | 63.8 | 0.331 |
| Reference | $Al_2O_3$ | 0.0285 | — | — | 177 | — | — | — | — |

EXAMPLE 2

Hydrogenation of stearic acid was conducted under the following conditions using catalyst A as prepared in Example 1.
Pressure: normal pressure
Temperature: 315° C.
Space Velocity of Acid (LHSV): 0.11 hr$^{-1}$
Space Velocity of Hydrogen (GHSV): 1,250 hr$^{-1}$ As a result, the conversion of stearic acid was 91.7%, the selectivity of stearic aldehyde was 84.6%, the space time yield of stearic aldehyde was 0.33 mol/kg-catalyst·hr.

EXAMPLE 3

Hydrogenation of n-octanoic acid was conducted under the following conditions using catalyst A as prepared in Example 1.
Pressure: normal pressure
Temperature: 330° C.
Space Velocity of Acid (LHSV): 0.11 hr$^{-1}$
Space Velocity of Hydrogen (GHSV): 1,250 hr$^{-1}$ As a result, the conversion of n-octanoic acid was 96.9%, the selectivity of n-octanal was 72.9%, and the space time yield of n-octanal was 0.57 mol/kg-catalyst·hr.

EXAMPLE 4

Hydrogenation of pivalic acid was conducted under the following conditions using catalyst A as prepared in Example 1.
Pressure: normal pressure
Temperature: 340° C.
Space Velocity of Acid (LHSV): 0.13 hr$^{-1}$
Space Velocity of Hydrogen (GHSV): 400 hr$^{-1}$ As a result, the conversion of pivalic acid was 97.0%, the selectivity of pivalic aldehyde was 99.5%, and the space time yield of pivalic aldehyde was 1.1 mol/kg-catalyst·hr.

EXAMPLE 5

Hydrogenation of cyclohexanecarboxylic acid was conducted under the following conditions using catalyst A as prepared in Example 1.
Pressure: normal pressure
Temperature: 330° C.
Space Velocity of Acid (LHSV): 0.097 hr$^{-1}$
Space Velocity of Hydrogen (GHSV): 1250 hr$^{-1}$ As a result, the conversion of cyclohexanecarboxylic acid was 97.1%, the selectivity of cyclohexanecarbaldehyde was 98.9%, and the space time yield of cyclohexanecarbaldehyde was 0.70 mol/kg-catalyst·hr.

EXAMPLE 6

Hydrogenation of methyl stearate was carried out under the following conditions using catalyst A as prepared in Example 1.
Pressure: normal pressure
Temperature: 310° C.
Space Velocity of Ester (LHSV): 0.12 hr$^{-1}$
Space Velocity of Hydrogen (GHSV): 1250 hr$^{-1}$ As a result, the conversion of methyl stearate was 83.0%, the selectivity of stearic aldehyde was 72.6%, and the space time yield of stearic aldehyde was 0.23 mol/kg-catalyst·hr.

COMPARATIVE EXAMPLE 3

Hydrogenation of cyclohexane carboxylic acid was conducted in the same manner as in Example 5, except for using catalyst B and at the temperature of 350° C.

As a result, the conversion of cyclohexane carboxylic acid was 92.9%, the selectivity of cyclohexanecarbaldehyde was 96.4%, and the space time yield of cyclohexanecarbaldehyde was 0.60 mol/kg-catalyst·hr.

As described in the foregoing, an aliphatic or alicyclic aldehyde can be produced in high yield directly from a corresponding aliphatic or alicyclic carboxylic acid or a derivative thereof by the process according to the present invention.

While the invention has been described in detail and with reference to specific examples thereof, it will be apparent to one skilled in the art that various changes and modifications can be made therein without departing from the spirit and scope thereof.

What is claimed is:

1. A process for producing an aliphatic or alicyclic aldehyde comprising the step of hydrogenating an aliphatic or alicyclic carboxylic acid or a derivative thereof which will yield an aliphatic or alicyclic aldehyde, with molecular hydrogen in the presence of a catalyst.
    wherein said catalyst is a zirconium oxide catalyst which contains chromium as an essential component; has a weakly basic site amount of more than 0.03 mmol/g as determined by a temperature programmed desorption method using carbon dioxide as an adsorbate in which the amount of carbon dioxide desorbed in the temperature range of from 100° to 250° C. is measured; and has pores having a radius of from 20 to 500 Å in an amount of not less than 0.1 cc/g and pores having a radius of from 1,000 to 50,000 Å in an amount of not less than 0.05 cc/g as measured with a mercury porosimeter.

2. A process as claimed in claim 1, wherein said zirconium oxide catalyst is one prepared by the steps of: mixing a material comprising zirconium oxide which will yield zirconium oxide upon firing at 400° to 1,100° C. a chromium compound, and an organic binder removable on combustion; extrusion-molding the mixture; drying; and firing at 400° to 1,100° C., wherein said chromium compound is selected from the group consisting of chromium sulfate, chromium nitrate, chromium halide, chromium (VI) oxide, bichromic acid, an ammonium or alkali metal salt of the preceding chromium compounds, chromium formate, chromium acetate, chromium anhydride salts and chromium oxalate.

3. A process as claimed in claim 2, wherein said material comprising zirconium oxide which will yield zirconium oxide upon firing at 400° to 1,100° C. is selected from the group consisting of zirconyl hydroxide, zirconium hydroxide, zirconyl carbonate, and commercially available zirconium oxide.

4. A process as claimed in claim 2, wherein said chromium compound is selected from the group consisting of chromium sulfate, chromium nitrate, a chromium halide, chromium (VI) oxide, bichromic acid and an ammonium or alkali metal salt thereof, chromium formate, chromium acetate, and chromium oxalate.

5. A process as claimed in claim 2, wherein said material comprising zirconium oxide which will yield zirconium oxide upon firing at 400° to 1,100° C. and chromium compound are mixed at a Cr/Zr atomic ratio of from 0.001 to 0.5.

6. A process as claimed in claim 2, wherein said organic binder is selected from the group consisting of polyvinyl alcohol, starch paste, crystalline cellulose, a surface active agent, a low-melting wax, and stearic acid.

7. A process as claimed in claim 1, wherein said aliphatic or alicyclic carboxylic acid or a derivative thereof is selected from the group consisting of an aliphatic or alicyclic carboxylic acid which may have a reaction inert substituent, and an ester or anhydride thereof.

8. A process as claimed in claim 7, wherein said aliphatic carboxylic acid is a saturated or unsaturated carboxylic acid having from 4 to 24 carbon atoms.

9. A process as claimed in claim 7, wherein said alicyclic carboxylic acid is cyclohexanecarboxylic acid.

10. A process as claimed in claim 1, wherein said hydrogenating is carried out at a temperature of from 200° to 500° C.

11. A process as claimed in claim 1, wherein said catalyst is a fixed bed catalyst, said aliphatic or alicyclic carboxylic acid or a derivative thereof is fed at a liquid hourly space velocity of from 0.01 to 1 $hr^{-1}$, and hydrogen is fed at a gas hourly space velocity of from 100 to 20,000 $hr^{-1}$.

* * * * *